United States Patent [19]
Lanzara

[11] Patent Number: 5,597,699
[45] Date of Patent: Jan. 28, 1997

[54] METHOD FOR DETERMINING DRUG COMPOSITIONS TO PREVENT DESENSITIZATION OF CELLULAR RECEPTORS

[76] Inventor: Richard G. Lanzara, 30 W. 86th St.-1B, New York, N.Y. 10024

[21] Appl. No.: 407,911

[22] Filed: Mar. 21, 1995

Related U.S. Application Data

[63] Continuation-in-part of Ser. No. 188,951, Jan. 31, 1994, abandoned, which is a continuation of Ser. No. 954,865, Sep. 30, 1992, abandoned.

[51] Int. Cl.⁶ .................................................. G01N 33/567
[52] U.S. Cl. ........................ 435/7.21; 435/7.2; 436/501
[58] Field of Search ................................. 435/7.21, 7.2; 436/501

[56] References Cited

PUBLICATIONS

Fernandes et al., "B–Adrenoceptordesensitization in guinea–pig etc. . . ", European Journal of Pharmacology, 157:135–145, 1988.

Dilger et al, "Direct Measurement . . . Channel"; Biophys. J Biophysical Society; vol. 57(Apr.):723–731, 1990.

Geoffroy et al; "Reduction of Desensitization . . . by Antagonists"; Molecular Pharamacology, 39:587–591, 1991.

Stephenson—A modification of Receptor Theory—; Brit. J. Pharmacol., 11, 379–393, 1956.

Keen—Testing Models of Agonism for G protein—coupled receptors—; TIPS—vol. 12:371–375, 1991.

Colquhoun—Validity of the Operational Model; Trends in Pharm. Sci.(TIPS) vol. 10:17, 1989.

Primary Examiner—Mary E. Mosher
Assistant Examiner—Donna C. Wortman
Attorney, Agent, or Firm—Schmeiser, Olsen & Watts

[57] ABSTRACT

Drug compositions combining antagonists with agonists to prevent desensitization of cellular receptors. An agonist is a substance or drug that produces a maximal or nearly maximal response, whereas an antagonist is a substance or molecule that produces no response, but can block the action of the agonist/drug. A partial agonist produces a moderate response and can also block the response of the receptor to the agonist/drug. The instant invention solves the problem of determining the optimal concentration of an antagonist or inhibitor which is necessary to prevent desensitization, without causing unnecessary and unwanted inhibition, by providing a formulative method detailing how a competitive antagonist of the receptor should be combined with an agonist in a specific proportion to maximize and maintain receptor response throughout drug therapy/administration.

1 Claim, 4 Drawing Sheets

METHOD FOR DETERMINING DRUG COMPOSITIONS TO PREVENT DESENSITIZATION OF CELLULAR RECEPTORS

This application is a Continuation-in-Part of U.S. Ser. No. 08/188,951 filed on Jan. 31, 1994 by the same inventor, abandoned, which is a continuation of Ser. No. 07/954,865, filed Sep. 30, 1992, abandoned.

BACKGROUND OF THE INVENTION

1. Field of the Invention

This invention relates generally to drug compositions or formulations which have the capability of eliciting specific responses from cellular receptors and, specifically, to those optional compositions/formulations which prevent desensitization of such receptors.

2. Discussion of Relevant Art

Throughout this disclosure, I shall use terms with their generally accepted meanings and, on occasion, supplement those meanings as indicated in order to clarify a particular facet of my invention by concentrating on a specific relationship or agenda that is normally generalized by use of the term.

An agonist is a substance/drug that has affinity for and stimulates physiologic activity at cell receptors that are normally stimulated by naturally occurring substances. As used throughout, an agonist is such a substance/drug that produces a maximal or nearly maximal response, whereas an antagonist is a substance or molecule that produces no response, but can block the action of the drug-agonist. A partial agonist produces a moderate response and can also block the response of the receptor to the agonist-drug. A competitive antagonist is a substance which competes with the agonist for the receptor, but produces no response.

Present theories of receptor activation calculate the response of a receptor as some function of an agonist-receptor complex. There have been several modifications and criticisms of receptor theory (see, for example Keen, M.; Testing Models of Agonism for G-Protein Coupled Receptors: *Trends Pharmacol. Sci.* 12, 371–374, 1991), but none of these treatments examined the discrete change induced by ligand binding to two equilibrium states of a receptor and, consequently, no one has developed the instant (and exacting) method for determining actual drug compositions which effectively prevent desensitization of cellular receptors that are normally and incipiently responsive to a host of agonists. Careful experimental investigations of several different receptor systems have revealed that receptor theory fails to describe the observed responses in a number of cases. Also, the phenomenon of rapid desensitization has been difficult to model by modern receptor theories. Originally many of these experimental observations were reported in 1957 by del Castillo and Katz in their pioneering work on desensitization (del Castillo, J. and Katz, B. *Proc. Roy. Soc. Lond.* 146, 369–381, 1957). The present theories are inadequate for at least two fundamental reasons; first, they fail to describe experimental observations except for limited cases and second, they offer only a "black box" description instead of a physicochemical explanation for receptor response.

Recently, Geoffrey et al. found that competitive antagonists of a glutamate receptor decreased the desensitization of the receptor (See Geoffrey, M., et al. *Molecular Pharmacology* 39, 587–591; 1991). They concluded, in this study, that such paradoxical behavior could not be described by the current theories of pharmacologic action deriving from (for example) experimental observations first recorded in 1957 by del Castillo & Katz performing their pioneering work on desensitization. Until most recently, no theory has been able to adequately explain how the behavior observed by Geoffrey et al. occurs; and, the utility of mixing competitive antagonists (or partial agonists) with agonists accurately and, therefore, efficiently to prevent receptor desensitization has been all but overlooked.

Other articles which show the utility (in vivo) of using antagonist/agonist compositions, to prevent receptor desensitization, are extant. One such article is "Antitacyphylactic Effects of Progesterone and Oxytocin on Term Human Myometrial Contractile Activity In Vitro" by Xin Fu, MD, Masoumeh Rezapour, MD, Mats Löfgren, MD, PhD, Ulf ulmsten, MD, PhD, and Torbjörn Bäckström, MD, PhD, all of the Department of Gynecology and Obstetrics, University Hospital, Uppsala, Sweden and published in *Obstetrics & Gynecology* (1993; 82: 532–8). Therein, Xin Fu et al. conclude that a quantum of an antagonist, progesterone, is observed to reverse the tachyphylaxis (desensitization) to oxytocin (agonist) of human myometrium. No quantification methodology is suggested for arriving at proper dosages of the antagonist for consistently achieving this reversal, however.

Another disclosure is of certain importance in the quest for in vivo studies to support modeling investigational techniques in drug research: "$Beta_1$ and $Beta_2$ Adrenoceptors in the Human Heart: Properties, Function, and Alterations in Chronic Heart Failure" by Otto-Erich Brodde of Bio-chemisches Forschungslabor, Medizinische Klinik and Poliklinik, Abteilung für Nieren-und Hochdruckkrankheiten, Universitätsklinikum, Essen, Germany. (*Pharmacologic Review*, 1991, Vol. 43, No. 2). This is a detailed study on chronic heart failure which discusses a recognized utility of using Beta-AR (beta-adrenergic receptor) antagonists for patients in certain types of heart failure (pp. 228–230) and which hypothesizes that such work by occupying Beta-ARs and prevent desensitization of cardiac Beta-ARs (see p.233 and references therein). No further information is detailed which would inform one of ordinary skill how to quantify the portions of antagonists necessary to fully retard i.e., prevent "down-regulation" (desensitization, ibid p. 233) of Beta-ARs. As recently as Jul. 24, 1994, the instant inventor presented his work "A Novel Biophysical Model for Receptor Activation" (R. Lanzara, CUNY, New York and BioBalance, Inc., New York, N.Y.) to the XIIth International Congress of Pharmacology at Montréal, Québec, Canada. Also presented was a paper published by him concerning Weber's Law ("Weber's Law Modeled by the Mathematical Description of a Beam Balance", *Mathematical Biosciences*, 122:89–94 (1994)). These works are included for their teachings on the instant concept, methods of calculation to provide quanta of antagonist: agonist necessary for achieving the objectives of the invention and demonstrate objectively by use of in vivo empirical studies that the invention is a substantial improvement to the prior art and a significant advancement in the field.

3.) Incorporation by Reference

The instant invention, being novel in its approach to solving the universally felt problem of drug receptor desensitization, is best appreciated with a thorough consideration of the works of the inventor and others. To this end, the following of the aforementioned works: Geoffroy et al. "Reduction of Desensitization of a Glutamate Ionotropic Receptor by Antagonists" *Molecular Pharmacology* 39:

587–91 (1991); Xin Fu et al., "Antitachyphylactic Effects of Progesterone and Oxytocin on Term Human Myometrial Contractile Activity In Vitro", *Obstetrics & Gynecology*, 82: 532–38 (1993); OttoErich Brodde, "Beta$_1$ and Beta$_2$ Adrenoceptors in the Human Heart: Properties, Function, and Alterations in Chronic Heart Failure", *Pharmocological Review*, Vol. 43, No. 2 (1991); Lanzara, R. "A Novel Bio-physical Model for Receptor Activation" Dept. of Allied Health Sci., CUNY, NY, N.Y. and BioBalance Inc., NY, N.Y.; and, Lanzara, R. "Weber's Law Modeled by the Mathematical Description of a Beam Balance", *Mathematical Biosciences*, 122: 89–94 (1994) are incorporated herein by reference.

SUMMARY OF THE INVENTION

Quite surprisingly, I have solved the problem of determining the optimal concentration of an antagonist or inhibitor which is necessary to prevent cellular receptor desensitization without causing unnecessary and unwanted inhibition. My formulation combines a competitive antagonist with an agonist for/of a particular receptor in a specific proportion that maximizes the receptor response to the agonist and maintains this maximum response. This formulation describes precisely the concentration of the antagonist relative to that of the agonist. This concentration is given by the dissociation constant of the antagonist, $K_i$, divided by the square root of one-half of the product of the two dissociation constants of the drug-agonist for the receptor. This is the fractional concentration of antagonist that is necessary to prevent any desensitization of the receptor. Higher concentrations of the antagonist may be used causing, however, more inhibition of the response. Lower concentrations of the antagonist may be used, but this would allow some desensitization to occur. Also, there is inherent in the aforementioned discoveries a method for calculating drug efficacy by utilization of easily identifiable biophysical parameters.

DETAILED DESCRIPTION OF THE PREFERRED EMBODIMENT

For all of the known receptors, most experimental observations have shown that agonist ligands display two-site binding while antagonist ligands display one-site binding. The experimental observations can be understood as a preferential binding of the agonists for one form of the receptor. This gives rise to the observed two-site binding and the two dissociation constants of the drug for the receptor. This is demonstrated to be a direct consequence of the efficacy of the agonist and is a measure of the response of the system. By this reasoning, antagonists would display equal or nearly equal affinities for each form of the receptor. This is observed as one-site binding and a single dissociation constant for antagonist binding to receptors.

Figure 1:
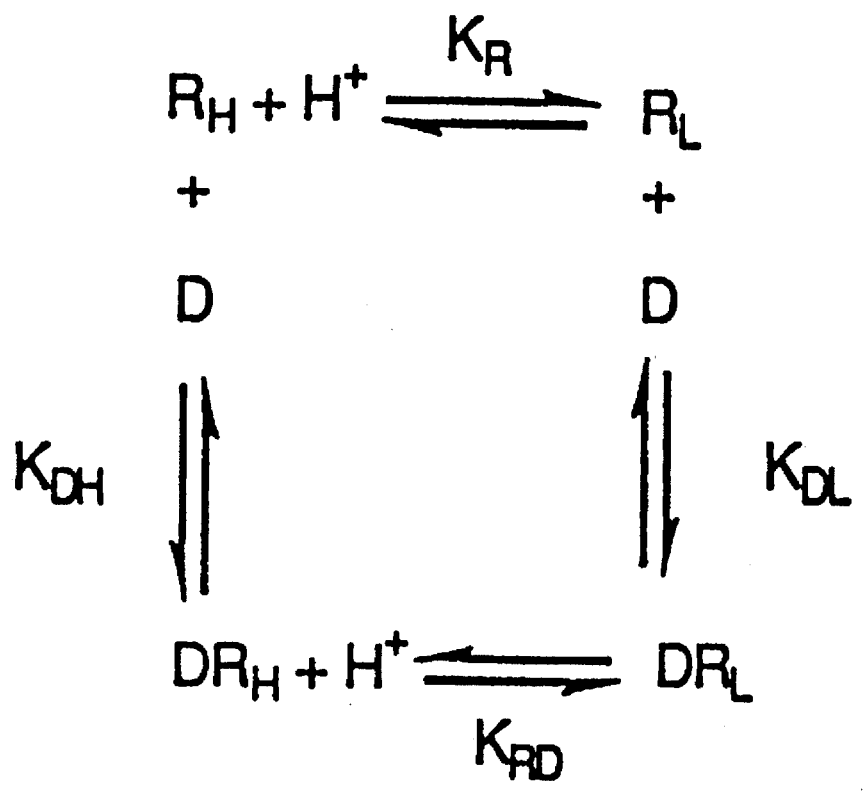
FIG. 1 depicts ligand equilibria with the ionic forms of the receptor.

For a receptor which exists in two states, an ionizable receptor was selected as a likely example because there is experimental evidence to support this. (See: Davies, A. O. *J. Clinical Endocrinology & Metabolism* 59, 398–405 (1984); Gende, O. A., Hurtado, M. C. C. & Cingolani, H. E. *Acta Physiol. Pharmacol. Latinoam.* 35, 205–216 (1985); Hall, M. D., et al. *Neurochemical Research* 11, 891–912 (1986); Asselin, J., et al. *Biochem. J.* 216, 11–19 (1983); Barlow, R. B. & Hamilton, J. T. *Brit. J. Pharmacol* 18, 543–549 (1962); Battaglia, G., Shannon, M., Borgundvaag, B. and Titeler, M. *Life Sciences* 33, 2011–2016 (1983); and Rocha E. Silva, M. *Arch. Int. Pharmacodyn.* 128, 355–374 (1960)). In FIG. 1, the equilibria of the ligand with the ionic forms of the receptor are shown. The two free forms of the receptor ($R_H$ and $R_L$) which can exist in either an ionized ($R_H$) form or a non-ionized ($R_L$) form, respectively, react with the drug D, with two different dissociation constants, $K_{DH}$ and $K_{DL}$; $DR_H$ and $DR_L$ are the amounts of the drug-receptor complex in either the high affinity or low affinity forms, respectively. The drug-receptor complex can also exist in either an ionized ($DR_H$) form or non-ionized ($DR_L$) form. The non-ionized form is the lower affinity form. This characterization teaches that the protonation of at least one (class of) residue within the receptor alters the affinity of the drug for the two free states of the receptor. The $K_R$ term is the dissociation constant of the hydrogen ion (H$^+$) binding to the receptor in the absence of the drug. The $K_{RD}$ term is the dissociation constant of hydrogen ion (H$^+$) binding to the receptor in the presence of the drug.

The drug (or ligand) binding to each of the two receptor states can be described by the Langmuir binding expressions.

$$DR_H = \frac{R_H(D)}{(D) + K_{DH}}$$

and $$DR_L = \frac{R_L(D)}{(D) + K_{DL}}$$

where $DR_H$ and $DR_L$ are the amounts of the drug-receptor complex for the high and low affinity states respectively and $R_H$ and $R_L$ are the total amounts of the receptors in the high and low affinity states. The ligand will have a preference for binding to the high affinity receptor state, $R_H$, over the low affinity receptor state, $R_L$, which is a direct result of the different dissociation constants $K_{DH}$ and $K_{DL}$.

Now introducing a new term, $\Gamma$, as a ratio of the high affinity states of the receptor to the low affinity states, the following expression is obtained:

$$\Gamma = \frac{R_H + DR_H}{R_L + DR_L} \quad [1]$$

where $\Gamma$ is a "weighted ratio" of the two receptor states. By substituting the binding expressions for $DR_H$ and $DR_L$ the complete expression for $\Gamma$ can be described as:

$$\Gamma = \frac{R_H(1 + (D/(D + K_{DH})))}{R_L(1 + (D/(D + K_{DL})))} \quad [2]$$

The derivation of equation [2] includes the assumption that the concentrations of the free receptor states ($R_H$ and $R_L$) are determined by the environmental influences on the protonation and deprotonation of the receptor and that the drug binding to each state can be described by Langmuir binding.

Perhaps the closest physical analogy to elucidate this "weighted ratio" approach is that the receptor equilibrium may be considered analogous to a beam balance with weights. The addition of a ligand is comparable to the addition of weights to each side of the balance relative to a hypothetical affinity with one side having the more weight or "higher affinity". The weighted ratio would be the ratio of the original weight plus the additional weight on the "high affinity" side of the fulcrum divided by the original weight plus the additional weight on the "low affinity" side. Additionally, a second weighted ratio would be the distances of the centers of mass from the fulcrum. This second weighted ratio would comprise the original distances plus or minus the change in these distances that was necessary to maintain the horizontal equilibrium point. The two weighted ratios will be equivalent and similar to this analysis of the receptor response.

Similarly a second or parallel determination of $\Gamma$ can be made from consideration of the conservation of matter law. This requires that any discrete change or increase (+x) in the high affinity state must be reciprocated by an equal and opposite change (−x) in the low affinity state with all receptor states equal to the total number of receptors ($R_T$). In this case, the equation for mass balance can be expressed as:

$$R_T = (R_H + x) + (R_L - x) \quad [3]$$

Now the weighted ratio of the high to low affinity states can be alternatively expressed as:

$$\Gamma = \frac{R_H + x}{R_L - x} \quad [4]$$

Equation [4] can be solved for the discrete change, x, which yields equation [5]:

$$x = \frac{\Gamma R_L - R_H}{1 + \Gamma} \quad [5]$$

The equivalence of equations [1] and [4] was tested numerically (not shown); also the expression for $\Gamma$ from equation [1] can be substituted into equation [5] and subsequently into equation [4] to produce the original expression for $\Gamma$.

To my knowledge, equating the weighted ratios of the high and low affinity receptor states in terms of the ligand binding or the conservation of matter law has never been done before. The novelty of this approach may appear awkward; however, the utility of such an approach will become evident for the routineer. Therefore, equating the two weighted ratios, equations [2] and [4], and solving for x yields:

$$\Delta RH = \frac{R_H R_L (D)(K_{DL} - K_{DH})}{R_L(2D + K_{DL})(D + K_{DH}) + R_H(D + K_{DL})(2D + K_{DH})} \quad [6]$$

where $\Delta RH$ is substituted for x, in order to emphasize that it represents the change in the high affinity state.

Taking the first derivative of the above equation with respect to the dose, D, and setting it equal to zero in order to obtain the peak (maximum) curve yields the following expression for the concentration of the drug where this peak occurs:

$$D = (K_{DH} K_{DL}/2)^{1/2} \quad [7]$$

In the presence of an antagonist or inhibitor (I), the equilibrium constants, $K_{DH}$ and $K_{DL}$, will each be multiplied by $(K_i + [I])/K_i$ so that equation (7) becomes:

$$D = (K_{DH} K_{DL}/2)^{1/2} (K_i + [I])/K_i \quad [8]$$

If the concentration of the inhibitor is expressed as a fraction of the dose of the drug ($[I] = f[D]$), then substitution of this expression for [I] into equation (8) and solving for f yields:

$$f = K_i(D - \Phi)/\Phi D \quad [9]$$

Where, $$\Phi = (K_{DH} K_{DL}/2)^{1/2}$$

Observing that equation (9) gives the minimal fractional concentration of the inhibitor with respect to the drug that is necessary to prevent the desensitization of the receptor, it follows that as [D] becomes much larger than $\Phi$, equation (9) becomes:

$$f = \frac{K_i}{\Phi} \quad [10]$$

This is the fractional dose of the antagonist relative to the concentration of the agonist or drug which is necessary and sufficient to prevent any desensitization of the receptor for the particular drug that is being used.

The instant formulation determines the lowest acceptable dose of inhibitor or antagonist to mix with the drug which completely prevents desensitization. It expresses the dose of inhibitor as a fraction of the dose of the drug. Further, the formulation prevents significant inhibition of the response at lower concentrations of the drug, yet prevents any of the desensitization of the receptor which is a direct result of the high concentrations of the drug (see FIG. 2).

Figure 2:
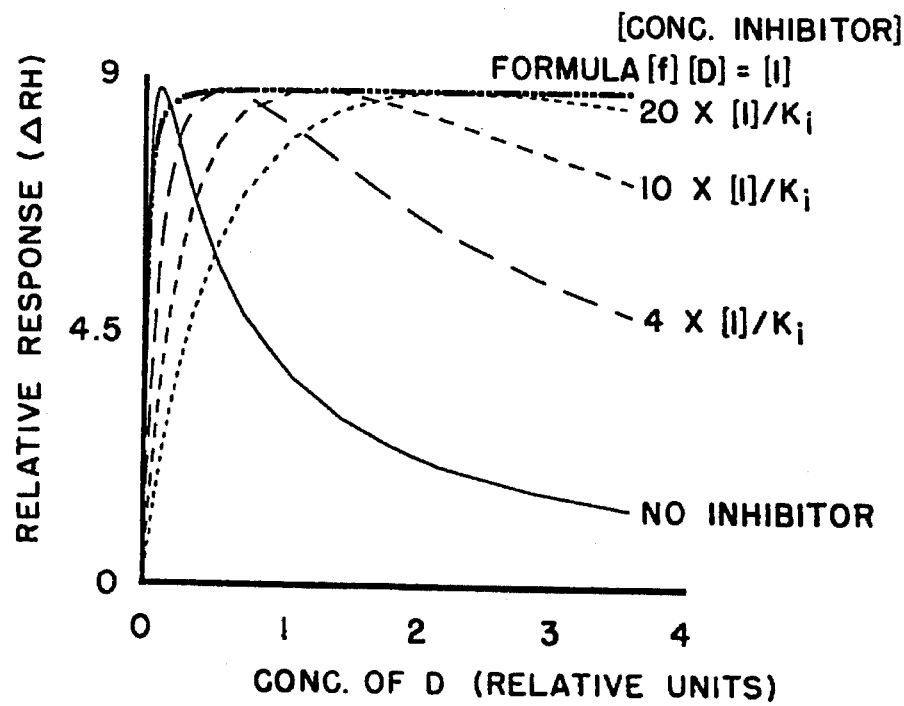
FIG. 2 is a graphical representation of Relative Response vs. Concentration for Different Concentrations of the Competitive Inhibitor, [I]

Referring particularly to FIG. 2 there is shown a graphical demonstration of the ability of the formulation fD=I to prevent desensitization without affecting the maximum response. Experimentally, computer simulations were carried out to demonstrate the ability of this model, equation [6], to describe a number of dose-response curves that were difficult or impossible to model by previous theories. Previously published experiments were compared to the predictions from this model. As an example, the experimental dose-response curves from del Castillo and Katz were described by equation (6) with and without an inhibitor (see FIG. 6).

Other experimentally determined curves have been described by my method including the more recent work of Keen (Keen, M., *Trends Pharmacol. Sci.* 12, 371–374 (1991)). The response curves from Keen are given in FIG. 4, wherein the darker curves are the computer generated curves from the model and fit those curves from the experiments and, whereas the lighter curves (generated from the prevalent operational model) failed to fit the experimental curves. Examples follow hereinafter in more detail, illustrative of the experimental development of my invention.

EXAMPLE 1

Stephenson's data (Stephenson, R. P., *British. J. Pharmacol.* 11, 379–393 (1956)) are presented in FIG. 3. The points on these curves were generated by equation [6]. The value for both of the $R_H$ and $R_L$ terms was 50 and the values of the pairs of $K_{DH}$ and $K_{DL}$ terms were as follows: Butyl ($3\times10^{-6}$, $8\times10^{-2}$); Hexyl ($5\times10^{-6}$, $2\times10^{-3}$); Ethyl ($1\times10^{-4}$, $1\times10^{1}$); Heptyl ($2\times10^{-5}$, $3\times10^{-4}$); Octyl ($3\times10^{-5}$, $2\times10^{-4}$); Nonyl ($4\times10^{-5}$, $2\times10^{-4}$); and Decyl ($3\times10^{-5}$, $2\times10^{-4}$). The concentration of drug [D] is represented on the abscissa in a molar log scale.

The reader will note that equation [6] can represent the experimental data from Stephenson with meaningful physicochemical parameters (i.e. the two dissociation constants of the drugs for the two receptor states).

EXAMPLE 2

Referring once again to FIG. 4, the plots of ΔRH (equation [6]—solid lines) for the data of Keen (Keen, 1991) are presented for arecoline, pilocarpine and carbachol as well as the plots of the operational model (broken lines). ΔRH was calculated with 300 as the value for the $R_H$ and $R_L$ terms to scale the curves appropriately. The $K_{DH}$ and $K_{DL}$ terms were varied in order to model the experimental curves. The $K_{DH}$ and $K_{DL}$ values for arecoline were 2 and 2000 respectively; similarly, the values for pilocarpine were 4 and 220; and the values for carbachol were 0.02 and 1000.

The Equation to Calculate the Curves for the Operational Model:

$$\% \text{ response} = \frac{\alpha([R_0]/K_{AR})(D/K_A)}{1 + (1 + ([R_0]/K_{AR}))(D/K_A)}$$

where represents agonist parameters and R receptor and $([R_0]/K_{AR})$=16, 7.3, 3.5, 1.3 and 0.116 with $\alpha$=100% (plotted as the broken lines in the graph). $K_A$ is the overall dissociation constant for the binding of the agonist to the receptor as defined in the operational model.

Figure 3:
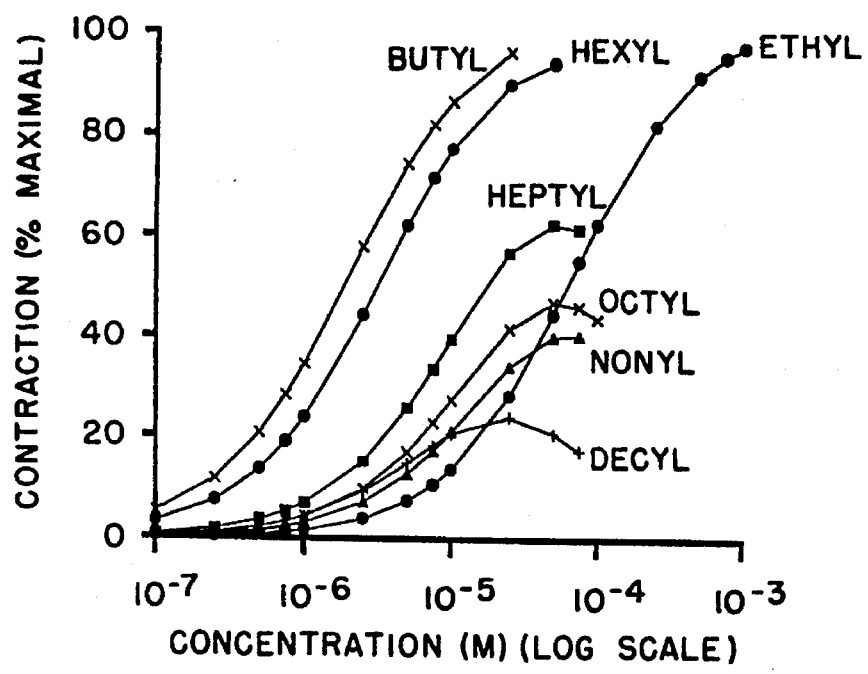
FIG. 3 reflects curves for the responses as determined by Stephenson.
Figure 4:
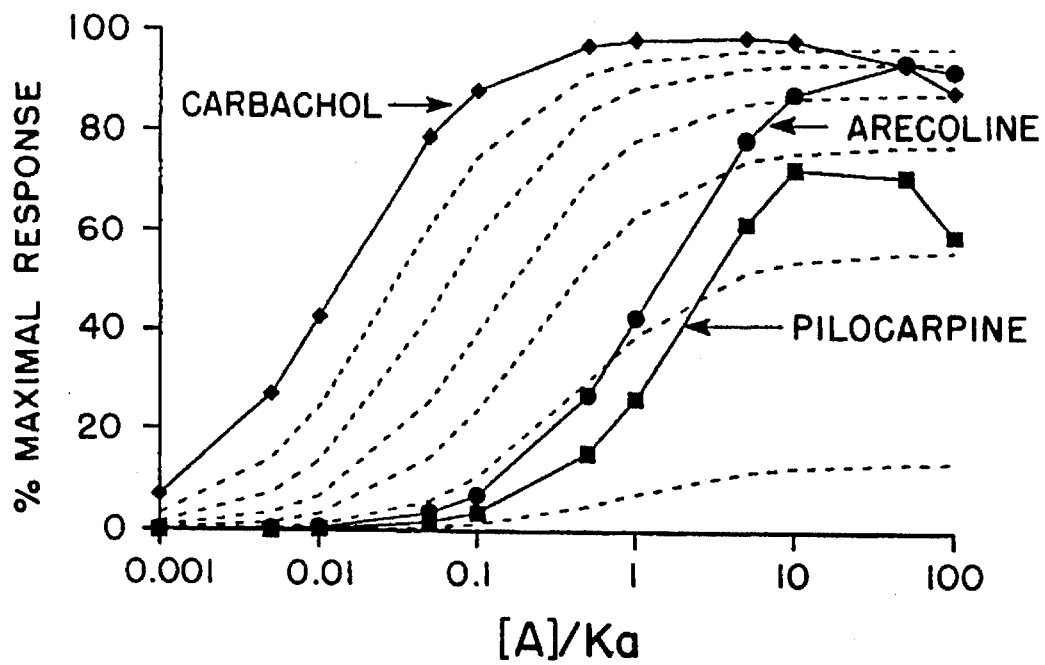
FIG. 4 is a model of ΔRH to the operational model and the data of Keen.

Experimentally determined response curves were examined to test the ability of ΔRH to model these curves. The experimentally determined dose-response curves from Keen (Keen, 1991) and Stephenson (Stephenson, 1956) were easily modeled by ΔRH from equation [6] with appropriately selected $K_{DL}$ and $K_{DH}$ values (FIGS. 3 and 4). Although there may be some tissue dependent effects from unstirred layers or diffusion barriers, no modifications were used in order to model these curves. Other curves were examined to test the ability of equation [6] to model these curves and to determine additional factors that may be necessary to model the total response.

Basically, there were two modifications to ΔRH that were necessary to model the experimental dose-response curves of Dilger and Brett (Dilger, J. P. and Brett, R. S., *Biophysical J.* 57, 723–731, (1990)) and del Castillo and Katz. The first modification was a diffusion equation to model the time-dependence of the ligand concentration at the receptors and the second modification was a "recruitment function" to model the concentration-dependent "diffusional recruitment" of additional receptors.

Most experimental preparations have multiple diffusion barriers or unstirred layers in the preparations which can cause time-dependent changes in the agonist concentration at the receptor sites. In order to account for this, the following diffusion equation was used:

$$[D]_t = \frac{(D)10^{(t^*Q/r^2)} - (D)}{10^{(t^*Q/r^2)}}$$

where $[D]_t$ is the time-dependent change in agonist concentration. (D) is the applied concentration of the agonist; "t" is the time; "Q" is the diffusion coefficient of the agonist and "r" is the estimated average diffusion distance. With $[D]_t$ substituted for (D) in equation [6], a time-dependent response could be modeled. The diffusion expression appears necessary to describe a time-dependence to the experimental curves, but not the overall shapes of these curves.

Because the peak heights of some experimental curves vary with the applied dose of agonist, an additional modification to ΔRH was necessary to model these curves. Application of high agonist concentrations produce large peaks, whereas, lower agonist concentrations produce small peaks in the measured dose-response curves. This is not predicted from plots of ΔRH with or without a diffusion equation. One explanation for this phenomenon is that there is a concentration-dependent "diffusional recruitment" of receptors. Katz and Thesleff (Katz, B. and Thesleff, S., *J. Physiol.* 138, 63–80 (1957)) and more recently Cachelin and Colquhoun (Cachelin, A. B. and Colquhoun, D., *J. Physiol.* 415, 159–188, (1989)) suggested that agonists may diffuse to distant receptors in their preparations and they proposed a concentration-dependent change in the total number of receptors as a necessary modification. The receptors which do not participate in the response at low agonist concentration may be either physically distant or separated by diffusion barriers within a particular preparation. This suggests that some of the receptors are removed from the initial site of agonist exposure but become "recruited" as the concentration of the agonist is increased. Because the experimental curves from Dilger and Brett have decreasing peak heights with decreasing agonist concentrations, a "recruitment function" was found necessary to modify ΔRH. This "diffusional recruitment" can be modeled approximately by a hyperbolic function which includes the ligand concentration and an apparent dissociation constant for the half maximal receptor recruitment.

$$R_F = \frac{R_M(D)}{(D) + K_F}$$

where $R_M$ represents the relative maximum number of receptors and $K_F$ is the apparent dissociation constant for the concentration of acetylcholine which produces a half maximum of the peak height. $R_F$ adjusted the relative number of receptors contributing to the total response by multiplying ΔRH times $R_F$.

EXAMPLE 3

Figure 5:
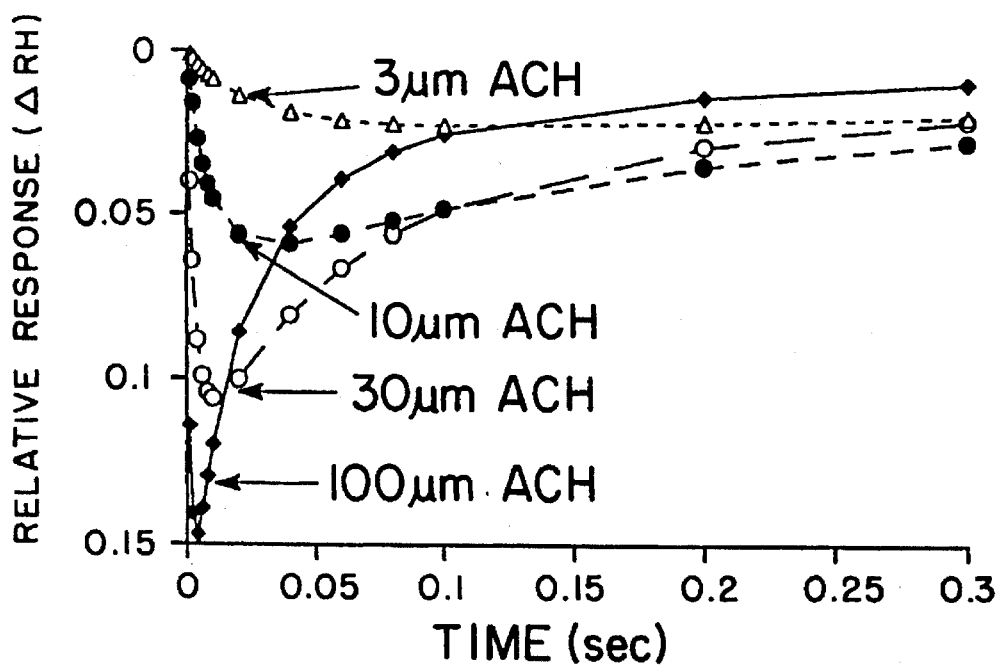
FIG. 5 is the response curves of Dilger and Brett modeled by ΔRH with a diffusion equation.

As depicted in FIG. 5, the response curves of Dilger and Brett are modeled by ΔRH with a diffusion equation, $[D]_t$, to represent the change in concentration with time and a recruitment function, $R_F$, to describe the diffusional recruitment of receptors. The diffusion coefficient used for acetylcholine (ACH) is $6\times10^{-10}$ m$^2$s$^{-1}$, which is a generally accepted value. The values for the $R_H$ and $R_L$ terms are one for this graph. The apparent affinity constant for the diffusional recruitment of receptors, $K_F$, is 20 µM as determined by the half maximal change in the peak heights of the experimental curves. Where "t" is the time in seconds and "900×10$^{-12}$" is the square of the distance (30×10$^{-6}$ m). The $K_{DH}$ and $K_{DL}$ values of acetylcholine are 0.01 and 0.1 respectively.

The series of equations to calculate ΔRH are:

$$R_F = \frac{100(D)}{(D) + K_F}$$

$$[D]_t = \frac{(D)10^{(t^*6\times10/900\times10)} - (D)}{10^{(t^*6\times10/900\times10)}}$$

$$DR_H = \frac{R_H[D]_t}{[D]_t + K_{DH}}$$

$$DR_L = \frac{R_L[D]_t}{[D]_t + K_{DL}}$$

$$\Gamma = \frac{R_H + DR_H}{R_L + DR_L}$$

$$\Delta RH = \frac{R_F(\Gamma R_L - R_H)}{1 + \Gamma}$$

where the last four equations are operationally equivalent to equation [6] for ΔRH.

The effect of a competitive inhibitor on the response curves can be modeled by including the expressions for competitive inhibition into the Langmuir binding expressions for $DR_H$ and $DR_L$ and then substituted into equation [5], so that the weighted ratio becomes:

$$\Gamma = \frac{R_H(1 + (D/(D + K_{DH}(1 + I/K_i))))}{R_L(1 + (D/(D + K_{DL}(1 + I/K_i))))}$$

where "$I/K_i$" is the concentration of the inhibitor divided by the dissociation constant of the inhibitor for the receptor. The effect of the competitive inhibitor on the response curve shows that when the inhibitor is present the slope of the response curve on the descending side diminishes more than the slope on the ascending side of the curve which is similar to the experimental observations of del Castillo and Katz as well as Geofroy et al.

EXAMPLE 4

Figure 6:
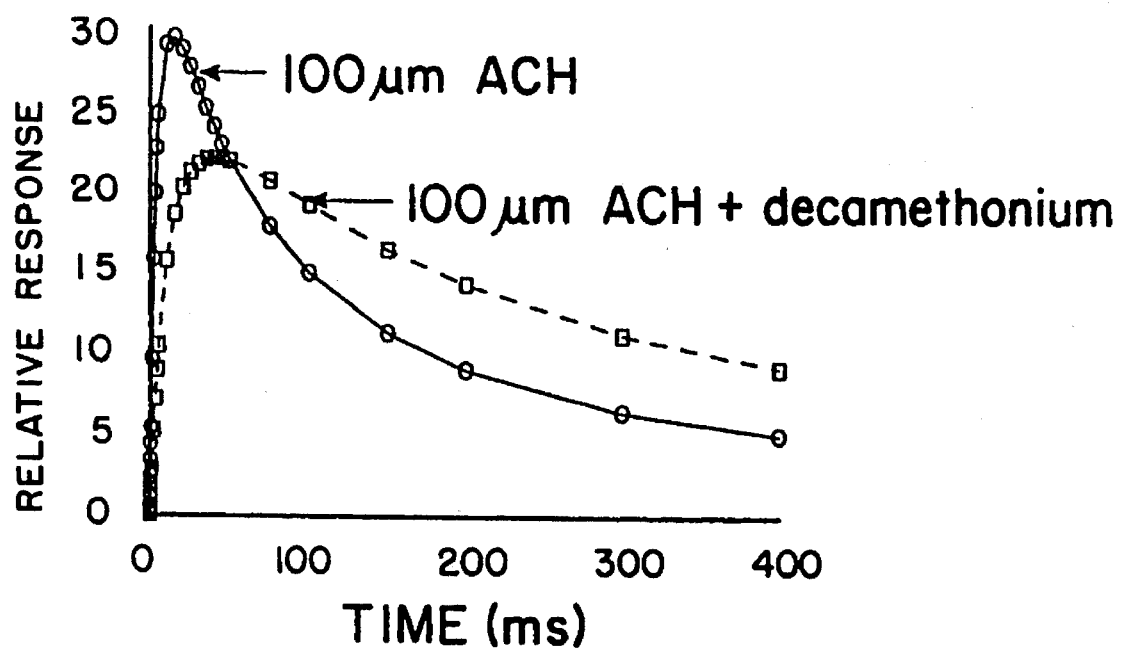
FIG. 6 is an experimental dual plot modeling of the del Castillo and Katz dose-response curves.

FIG. 6 consists in the two plots of ΔRH which model the experimental dose-response curves of del Castillo and Katz. ΔRH is computed by the series of sequential equations shown below. The values for the $R_H$ and $R_L$ terms are 100. The initially applied concentration of acetylcholine (ACH) was 100 μM. The values for the maximum peak response of acetylcholine (100 μM) and half maximal peak response (20 μM) were taken from Dilger and Brett for use in the recruitment function, $R_F$. The effective diffusion distance in [D]t is 191 μm and "t" is the time in seconds which is converted to milliseconds for the plot. The inhibitor concentration for decamethonium, expressed as $I/K_i$ is equal to either 0 or 1 ([I]=$K_i$) for the two plots.

The recruitment function, $R_F$, also includes the effect of the competitive inhibitor. Decamethonium, which was a weak partial agonist in the hands of del Castillo and Katz, is treated as a competitive antagonist without any contribution to the response.

The series of equations to calculate ΔRH:

$$R_F = \frac{200(D)}{(D) + K_F(1 + I/K_i)}$$

$$[D]_t = \frac{(D)10^{(t^*6 \times 10/364 \times 10)} - D}{10^{(t^*6 \times 10/364 \times 10)}}$$

$$DR_H = \frac{R_H[D]_t}{[D]_t + K_{DH}(1 + I/K_i)}$$

$$DR_L = \frac{R_L[D]_t}{[D]_t + K_{DL}(1 + I/K_i)}$$

$$\Gamma = \frac{R_H + DR_H}{R_L + DR_L}$$

$$\Delta RH = \frac{R_F(\Gamma R_L - R_H)}{1 + \Gamma}$$

To apply the instant methodology to a specific case requiring administration of a drug to a human subject according to a commonly accepted protocol (known in the art), one first obtains the drug's dose-response curve that is provided by the drug's maker. The curve is then "fitted" by normalizing for the total number of receptors and optimizing the values for the high and low affinity constants $K_{DH}$ and $K_{DL}$. These fitted values are the entering arguments for the calculation of Φ and f, according to this specification, which results in the fractional concentration of the inhibitor with respect to the drug-agonist (antagonist: agonist) that is necessary to prevent desensitization of the receptor. There exist, as a result of numerous in vivo studies and my in vitro models, several antagonist/agonist pairings: propranolol/isoproternol; atenolol/norepinephrine; 2-amino-5-phosphonopentanoic acid/N-methyl-D-aspartic acid; naloxone/morphine; progesterone/oxytocin and propanolol/terbutaline. The administration of antagonist is by normal delivery methods of its own character and may be done during the agonist administration or, if such is autonomic in the recipient, concurrent therewith, or shortly thereafter. It is also well known that agonists and antagonist can be made into pharmaceutical compositions by combinations with appropriate medical carriers or diluents. For example, such mixtures can be dissolved in oils, propyleneglycol, physiological saline, isopropyl myristate, ethanol, cremophor, glycol, sesame oil, or other such pharmacological solutions. Formulation as topicals is also available. Pharmacologists familiar with the panoply of drugs and their professional literature may readily use the invention with the guidance herein provided.

The methods which I have developed and teach may be applied by others in the field without departing from the spirit of the general invention. These methods and the compositions derived thereby are commended to others consistent with the hereinafter appended claims.

What is claimed is:

1. A method for making a composition that elicits a desired response from cellular receptors and prevents subsequent desensitization of said receptors, the method comprising the steps of:

selecting an agonist suitable for eliciting said response;

determining a first amount of the agonist effective for binding to said receptors in both a high and a low affinity state effective for obtaining said response;

selecting an inhibitor of said agonist specific to said receptors, said inhibitor selected from the group consisting of partial antagonists, antagonists, and competitive antagonists to the agonist;

determining a second amount of said inhibitor sufficient to prevent desensitization of said receptors, wherein said second amount is determined to be $K_i(K_{DL}K_{DH}/2)^{-1/2}$ of said first amount, where $K_{DL}$ and $K_{DH}$ are dissociation constants of said agonist in low and high affinity states, respectively, and $K_i$ is the dissociation constant of said inhibitor; and combining said second amount of said inhibitor with said first amount of said agonist to form a composition that elicits said desired response from cellular receptors and prevents subsequent desensitization of said receptors.

\* \* \* \* \*